US008038617B2

(12) United States Patent
Maschke

(10) Patent No.: US 8,038,617 B2
(45) Date of Patent: Oct. 18, 2011

(54) MOBILE DEFIBRILLATOR

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 603 days.

(21) Appl. No.: 11/481,664

(22) Filed: Jul. 6, 2006

(65) Prior Publication Data
US 2007/0038256 A1 Feb. 15, 2007

(30) Foreign Application Priority Data
Jul. 6, 2005 (DE) .......................... 10 2005 031 642

(51) Int. Cl.
*A61N 1/18* (2006.01)
*A61B 8/04* (2006.01)
*A61B 5/0402* (2006.01)

(52) U.S. Cl. ................. 600/439; 607/4; 607/5; 600/509; 128/916

(58) Field of Classification Search .................. 607/4, 5; 600/439, 509; 128/916
See application file for complete search history.

(56) References Cited

U.S. PATENT DOCUMENTS

| | | | | |
|---|---|---|---|---|
| 5,792,190 A * | 8/1998 | Olson et al. | ......................... | 607/5 |
| 5,853,005 A * | 12/1998 | Scanlon | ......................... | 600/459 |
| 6,023,638 A * | 2/2000 | Swanson | ......................... | 600/510 |
| 6,186,977 B1 * | 2/2001 | Andrews et al. | ................. | 604/67 |
| 6,287,328 B1 * | 9/2001 | Snyder et al. | .................. | 600/509 |
| 6,327,497 B1 * | 12/2001 | Kirchgeorg et al. | .............. | 607/3 |
| 6,397,104 B1 | 5/2002 | Miller et al. | | |
| 6,617,963 B1 * | 9/2003 | Watters et al. | .............. | 340/10.41 |
| 7,530,840 B2 * | 5/2009 | Lund et al. | ..................... | 439/501 |
| 2003/0020741 A1 | 1/2003 | Boland et al. | | |
| 2003/0130697 A1 * | 7/2003 | Halperin et al. | ................... | 607/3 |
| 2004/0127798 A1 * | 7/2004 | Dala-Krishna et al. | ........ | 600/450 |
| 2005/0043763 A1 | 2/2005 | Marcovecchio et al. | | |
| 2005/0107833 A1 * | 5/2005 | Freeman et al. | .................. | 607/5 |

OTHER PUBLICATIONS

Mark Damon Wheeler, "Automatic Modeling and Localization for Object Recognition", Carnegie Mellon University, Oct. 25, 1996, pp. 1-13, 1-13 and 110-119, CMU-CS-96-188, Pittsburgh, PA.
"Polygon", Wikipedia, Online, Retrieved on Apr. 19, 2006, pp. 1-3; URL: http://de.wikipedia.org/wiki/Polygon.

* cited by examiner

*Primary Examiner* — Carl H Layno
*Assistant Examiner* — Natasha Patel

(57) ABSTRACT

The invention relates to a mobile defibrillator which has a housing. In order to improve the diagnostic reliability, particularly in the case of irregular heart rhythms and myocardial infarctions, provision is additionally made for an imaging ultrasound device to be provided in or on the housing.

19 Claims, 2 Drawing Sheets

MOBILE DEFIBRILLATOR

CROSS REFERENCE TO RELATED APPLICATIONS

This application claims priority of German application No. 10 2005 031 642.5 filed Jul. 6, 2005, which is incorporated by reference herein in its entirety.

FIELD OF THE INVENTION

The invention relates to a mobile defibrillator.

BACKGROUND OF THE INVENTION

Such a defibrillator is disclosed in U.S. Pat. No. 6,397,104 B1, for example. The defibrillator makes provision for an electrocardiograph. The electrocardiograph allows the cardiac electric activity of a patient to be recorded. On the basis of the cardiac electric activity, it is possible to detect a cardiac arrest, ventricular fibrillation, irregular heart rhythms or myocardial infarctions. The known defibrillator has a disadvantage in that myocardial infarctions, in particular imminent or silent myocardial infarctions, cannot be dependably and reliably detected.

SUMMARY OF THE INVENTION

The invention addresses the problem of resolving the disadvantages inherent in the prior art. In particular, a mobile defibrillator will be specified which allows clinical conditions, in particular heart diseases and myocardial infarctions, to be diagnosed particularly quickly and reliably.

This problem is solved by the features in the Claims. Effective configurations of the invention are derived from the features in the Claims.

In accordance with the invention, provision is further made for an imaging ultrasound device in or on the housing. The ultrasound device allows imaging of internal tissues, organs, blood vessels and the like within the human body. On the basis of the ultrasound images, it is possible to detect clinical conditions, internal injuries, changes of internal tissues or blood vessels, etc. The ultrasound images make it easier to produce diagnoses particularly rapidly and reliably. Rapid production of reliable diagnoses is necessary for appropriate and rapid medical care in the case of medical emergencies. It is particularly important to detect irregular heart rhythms and myocardial infarctions dependably, and it is critically important to provide prompt and appropriate treatment, e.g. defibrillation. Using the ultrasound device, it is possible to detect changes of the heart tissue which cause a myocardial infarction, and to detect imminent and silent myocardial infarctions. This is even possible if electrocardiographic data shows no clinical symptoms or only very minor clinical symptoms.

The imaging ultrasound device can be contained within a housing. The defibrillator can be constructed such that it is particularly compact and robust. The ultrasound device can also be attached to the exterior of the housing, either permanently or detachably in the manner of a modular construction. The ultrasound device can be fastened to the housing using suitable fastening means, e.g. quick-release catches, snap-on catches and the like. The ultrasound device is preferably an integral component of the defibrillator and functionally coupled to the same. This allows a particularly compact and clear construction.

The power supply of an ultrasound device which is detachable from the housing can take place via cable or by means of electrical contacts which are provided on the ultrasound device. Provision can be made on the defibrillator for further contacts for the contacts. The further contacts can automatically create an electrical contact when the ultrasound device is attached to the housing. Connections for exchanging information between the ultrasound device and the defibrillator can be configured in a similar manner.

A monitor is preferably provided for imaging. The monitor can be integrated in the housing or contained in a recess of the housing. In order to align the display surface of the monitor with the field of view of the user, the monitor on the defibrillator can be attached rotatably about one or more axes. Provision is preferably made for a shared monitor for the defibrillator and the ultrasound device. The monitor can be a TFT monitor, LCD monitor or OLED (Organic Light-Emitting Diode) monitor.

According to a configuration of the invention, the monitor is a touch sensitive screen for manual initiation of functions of the defibrillator and/or ultrasound device. Using such a screen, it is possible to reduce the quantity and dimensions of operating panels which are attached to the housing. The housing and the defibrillator can be constructed in a particularly compact and clear manner. Using the touch-sensitive screen, it is also possible to offer a user assistance and selection help when initiating a function. The functions can be combined into menus. On the basis of menus, a selection of functions for operation and control of the defibrillator by the user can be provided for each operating mode. Incorrect operation can be avoided and it is possible to ensure particularly simple and dependable use of the defibrillator, in particular in emergency situations.

According to a further configuration of the invention, the ultrasound device features an ultrasound measuring head and a measured data processing unit, wherein measured data is transferred between the ultrasound measuring head and the measured data processing unit by means of a wireless connection. A wireless transfer ensures that it is possible to achieve a particularly high degree of freedom of movement and flexibility when using the ultrasound measuring head. Restrictions caused by cables can be avoided.

The measured data processing unit can be a digital circuit, a processor or the like. The measured data processing unit can be combined with or integrated in a control unit which is provided for controlling the defibrillator, a processor or the like. In particular, it is possible to provide a central control unit and/or measured data processing unit for the ultrasound device, the defibrillator and further medical entities which are provided with or connectable to the defibrillator, e.g. an electrocardiograph, a thermometer, a blood pressure measuring entity, etc.

According to a configuration of the invention, in or on the housing is a receptacle for holding a coupling substance for coupling a contact surface of the ultrasound measuring head to an examination object. The coupling substance can be held directly in the receptacle or in a tube or the like which is contained therein. The extraction of the coupling substance and the supply to the contact surface can be done manually, mechanically and/or electronically. The coupling substance can be carried via a tube from the receptacle to the ultrasound measuring head or to the contact surface. It is also possible for the receptacle to be provided in the ultrasound measuring head. As a result of providing the coupling substance at or with the defibrillator, the ultrasound device can be ready for operation particularly quickly.

According to an advantageous configuration of the invention, in or on the housing is an entity for capturing and/or processing and/or representing physiological data of a patient. The physiological data can be used in addition to the ultrasound data as supplementary information for producing a diagnosis. Particularly accurate and reliable diagnoses can be produced. The entity can be an electrocardiograph, a blood pressure measuring entity, a thermometer entity, etc. The entity or at least parts thereof can be permanently attached to the defibrillator or connectable thereto. In order to connect the entity/entities and associated measuring sensors, electrodes and the like, provision is made for corresponding connection interfaces preferably at an easily accessible location. A visual identification of different connection interfaces can be achieved by means of color codes and/or different geometries of the connection interfaces.

According to a further configuration of the defibrillator, means are provided for electrical isolation of electrically conductive elements of the entity and/or of the ultrasound device from defibrillator voltages and/or voltages of an electricity network which is connected to the defibrillator. As a result of electrical isolation, it is possible to prevent a user or patient from being unintentionally exposed to high defibrillator and/or electricity network voltages in the event of a defect. The electrical isolation is preferably achieved by means of visual separation.

A configuration of the invention provides for a connection interface for connecting an accumulator to a charge station, said accumulator being provided for supplying energy. Cables can be used for connecting to the charge station. At the defibrillator and at the charge station, provision can also be made for electrical contacts which automatically create an electrical contact when the defibrillator is placed in the charge station. Alternatively, the accumulator itself can also be placed into a charge station which is provided for this purpose. In this case, the defibrillator can be fitted with a further charged accumulator and is immediately ready for use again. Charging can be done via a public electricity network and/or via an electricity network which is provided in a motor vehicle.

According to a further configuration of the invention, provision is made for a data interface for exchanging data with a data processing system. The data processing system can be, for example, a hospital database system or data network for managing and/or providing patient data. The data can be patient data which is stored during treatment of a patient with the defibrillator. In particular, it can be physiological data, ultrasound data, defibrillation data and the like. The data can be used for further diagnostic purposes. The data interface can also be used to transfer software data for controlling the defibrillator, the ultrasound device and/or the entity/entities which are provided. A transfer of the data preferably takes place via a data interface which is selected from the following group: USB, RS232, radio, infrared, Firewire.

According to an advantageous configuration of the invention, in order to screen against external electromagnetic fields in the case of an electronic functional element of the defibrillator, provision is made at least partially for an outer layer featuring metallic particles, wherein the particles have an average diameter of less than 100 μm and preferably less than 100 nm. By virtue of such a layer, it is possible to screen control lines and signal lines and electronic functional elements and components of the ultrasound device, the entity/entities, the monitor, etc. against external electromagnetic fields. In particular, the electromagnetic fields that occur during a defibrillation can be screened. Adverse effects caused by electromagnetic fields can be effectively prevented.

According to a further configuration of the invention, provision is made for a transponder, preferably an RFID transponder. By virtue of the transponder, the defibrillator can be unambiguously identified using a readout device. The transponder can be provided in or on the housing. Provision can also be made for a plurality of transponders. For example, transponders can be provided in each case for components which are separable from the defibrillator, e.g. electrodes, measuring sensors, etc. The latter can be unambiguously assigned to an associated defibrillator on the basis of the information which is stored on the transponder in each case. Data such as an identification number, the owner, the customary location, for example, and technical data such as age, service interval and operating data can be stored on the transponder. In public installations which have permanently installed readout entities for transponders, e.g. in airports, train stations, subways, hospitals, etc., the transponder can also be used for specifying the location or current point of use of the defibrillator. Knowledge of the location allows particularly rapid provision of primary and secondary medical care in the event of an emergency.

According to a configuration of the invention, a readout unit is provided for reading out information which is stored on a further transponder. The further transponder can be a transponder which is allocated to a patient in a hospital. The transponder which is allocated to the patient can be attached to a patient bed or to the patient by means of an armband or the like. Patient data and medical data can be stored on the transponder. The readout unit is particularly suitable for medical installations, e.g. hospitals and care homes. The patient data is quickly available and can be displayed on the monitor of the defibrillator.

According to a further configuration of the invention, a card reader is provided for reading out patient data which is stored in a memory on a patient card. The patient card can be a conventional sickness insurance card. The patient data which is read out can be displayed on the monitor and/or stored with the data which is recorded by the defibrillator. The stored data can subsequently be assigned to the patient unambiguously on the basis of the patient data.

According to a particularly advantageous configuration of the invention, a communication device selected from the following group is provided for transferring information via a telephone connection: mobile telephone, fax device, modem. The communication device allows a transfer of data which is recorded or captured using the defibrillator, e.g. patient data, physiological data, ultrasound data etc. The information can be transferred to a hospital, for example. In the hospital, the information can be used for preparing secondary medical care or for further treatment. In particular, the communication device can be a bidirectional communication device. An emergency call routing center, a hospital and the like can be informed or contacted directly from a point of use. Furthermore, an additional emergency call entity for generating and sending an emergency call signal can be provided at the defibrillator.

According to a configuration of the invention, a navigation system is provided for determining the position of the defibrillator. The navigation system can be used to ascertain the exact position of the defibrillator. On the basis of the ascertained position, further emergency services, ambulances and the like can be dependably and reliably routed to a point of use. The navigation system can also be used for providing a route description to the point of use. The navigation system can be a satellite-based navigation system. It can also be a navigation system in which position data is received and transmitted via a radio connection to local permanently installed node points. The latter is particularly advantageous in the case of underground installations such as, for example, subway stations or buildings in which satellite-based navigation is not possible. In the case of the navigation system, provision can also be made for a combination of the satellite-based navigation and the navigation which is based on a radio connection with node points.

BRIEF DESCRIPTION OF THE DRAWINGS

Advantageous configurations of the invention are explained in further detail below with reference to the drawings, in which.

DETAILED DESCRIPTION OF THE INVENTION

Figure 1:
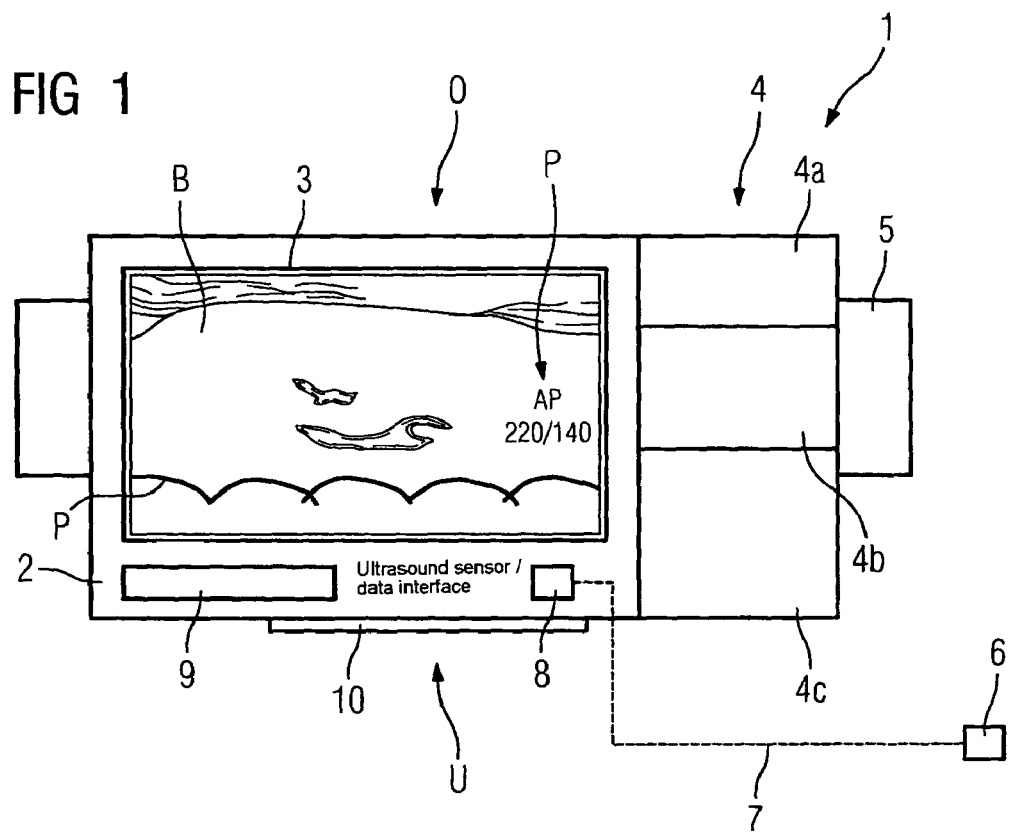
FIG. 1 schematically shows a defibrillator according to the invention.

FIG. 1 schematically shows a defibrillator 1 in accordance with the invention. The defibrillator 1 has a housing 2 and a monitor 3 of an ultrasound device, said monitor being attached at a top side O. Ultrasound images B and/or physiological data P can be displayed on the monitor 3. In addition to the monitor 3, provision is made for an operating panel 4 for initiating functions of the defibrillator 1, functions of the ultrasound device and functions of further entities for capturing physiological data. The operating panel 4 has a first section 4a for operating and controlling the defibrillator, a second section 4b for operating and controlling the ultrasound device and a third section 4c for operating and controlling further entities such as, for example, an electrocardiograph, a blood pressure measuring entity, a thermometer entity and the like. Attached to the housing 2 on two opposite sides are two defibrillator electrodes 5 for applying an electric shock to a patient. An ultrasound measuring head 6 is provided for recording ultrasound measurement data. The ultrasound measurement data is transferred from the ultrasound measuring head 6 to a data interface 7 via a radio connection 8. However, the ultrasound measurement data can also be transferred via a cable. In a recess of the housing 2, interfaces 9 are provided for connecting the entities and for exchanging data with an external data processing system which is not shown. A connection interface 10 for the connection of an accumulator to a charge station (not shown) is provided at a bottom side U of the defibrillator 1, said accumulator being provided for supplying energy in the housing 2.

Figure 2:
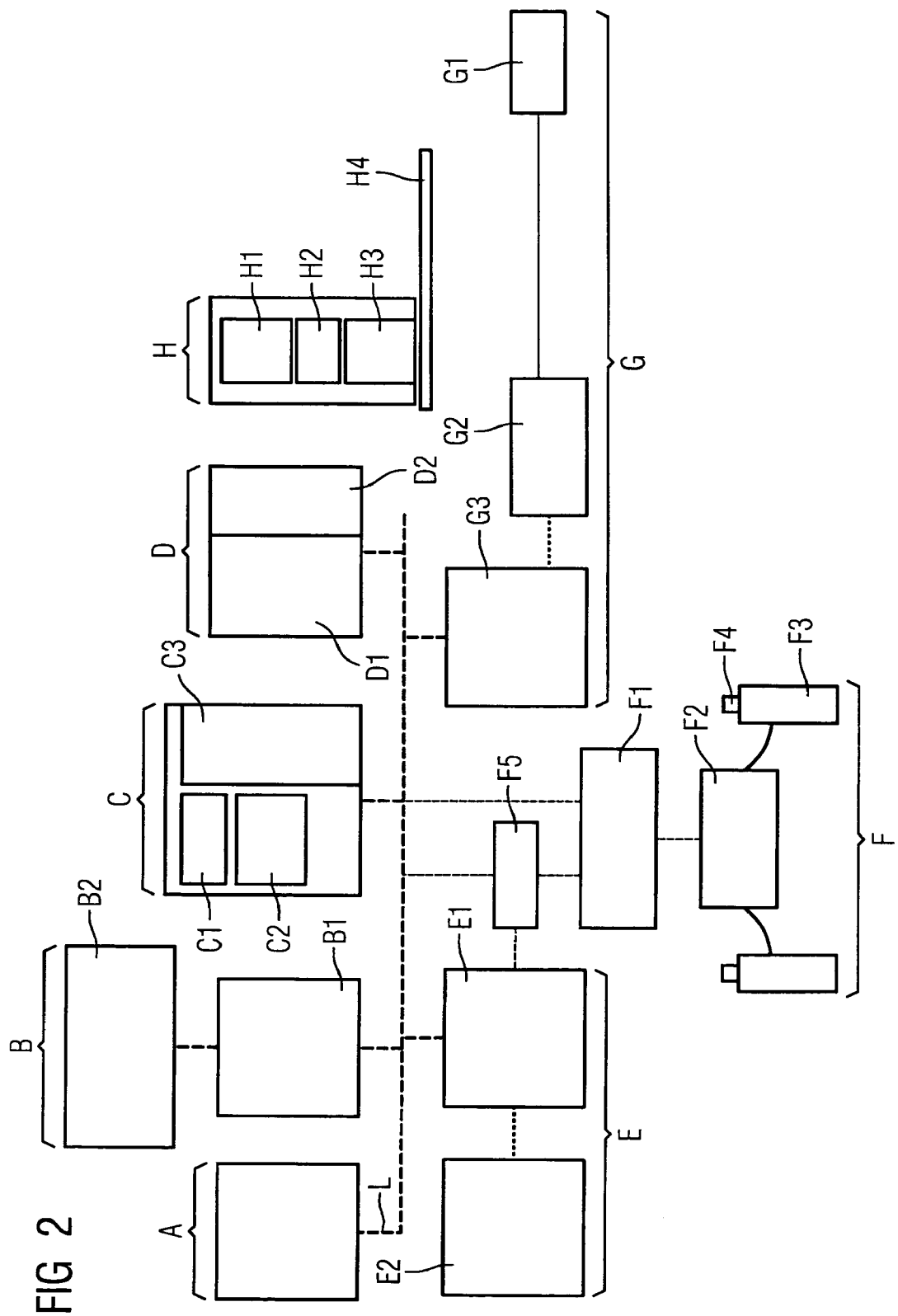
FIG. 2 shows a block diagram of the defibrillator from FIG. 1.

FIG. 2 shows a block diagram of the defibrillator 1 from FIG. 1. The defibrillator 1 has a microprocessor block A, a display block B, an input/output block C, a memory block D, a patient monitoring block E, a defibrillation block F, an ultrasound block G and an energy supply block H. The blocks A to G are connected together via a bus cable L for the transfer of energy and/or data.

The display block B features a display control unit B1 for controlling a display B2 for physiological data, patient data, ultrasound data and/or defibrillation data. The display B2 contains the monitor 3 which is shown in FIG. 1 and can include further display elements such as, for example, LEDs, displays, status indicators etc. The input/output block C features a defibrillator menu C1, a patient monitoring menu C2 and an ultrasound menu C3. The memory block D comprises a first memory area D1 for storing patient data, physiological data and operating data of the defibrillator, and a second memory area D2 for storing ultrasound data. The patient monitoring block E features a signal processing unit E1 for processing patient monitoring data. For the purpose of capturing the patient monitoring data, a sensor unit which is designated as E2 features one or more sensors, electrodes etc. The defibrillation block F features a defibrillation control unit F1 and an associated high-voltage unit F2. Defibrillator electrodes F3 are connected to the high-voltage unit F2. An initiator switch F4 is provided at each defibrillator electrode F3 for initiating a delivery of an electric shock via the defibrillator electrodes F3. The initiator switch F4 can be developed such that the danger of an unintentional delivery of an electric shock is reduced. For example, provision can be made that simultaneous depression of both initiator switches F4 is required in order to deliver an electric shock. The defibrillation block F also features a synchronization unit F5 for synchronizing the delivery of the electric shock with the electrocardiographic data. The ultrasound block G comprises an ultrasound measuring head G1 and an ultrasound data interface G2 which is connected to the ultrasound measuring head G1 and via which ultrasound measurement signals are transferred to an ultrasound signal processing unit G3. The energy supply block H features an accumulator H1, a voltage transformer H2 for converting the output voltage of the accumulator H1 and a power connection interface H3 for the connection of a charge station H4 for charging the accumulator H1.

The function and the interaction of the blocks of the defibrillator are as follows:

The microprocessor block A contains at least one microprocessor for controlling, monitoring and/or managing individual components of the defibrillator 1. The components can be any components of the blocks A to G. In particular, they can be the first memory area D1 and second memory area D2, the display B1, the sensor unit E2, etc. In order to exchange data between the blocks A to G, these are connected together via the bus cable L. The blocks A to G are connected to the energy supply block H via a cable connection (not shown) for the supply of power. The output voltage of the accumulator H1 is adapted by means of the voltage transformer H2 to operating voltages which are required in each case for individual blocks and their components. In order to charge the accumulator H1, a charge socket H3 is provided for connection to the charge station H4. The charge socket H3 is advantageously provided at a bottom side of the defibrillator 1. In order to charge the accumulator H1, the defibrillator 1 with the charge socket can be inserted into a holder of the charge station H4. Electrical contacts can be provided at the charge socket and the charge station H4. A transfer of energy from the charge station H4 to the defibrillator 1 can also take place in a contactless manner, e.g. by means of an electromagnetic coupling. The electrical contacts automatically create an electrical contact upon insertion in the charge station H4. The accumulator H1 is charged immediately after insertion. It is also possible for the accumulator H1 to be removed from the defibrillator 1 and inserted in an accumulator charge station which is provided for this purpose. In this case, an empty accumulator H1 can be replaced by a further charged accumulator. This can improve the operational readiness of the defibrillator 1.

The patient monitoring block E is provided for capturing physiological data of a patient. Using this data, clinical conditions can be diagnosed more easily in conjunction with ultrasound data. The data can be electrocardiographic data, oxygen saturation data, blood pressure data and/or temperature data. The sensor unit E2 can include corresponding known electrodes and/or sensors for capturing the data. Connection interfaces or interfaces 9 are provided for connection of the electrodes and/or sensors are provided on the housing 2 of the defibrillator. In order to identify individual connection interfaces, these are assigned an unambiguous color code. In order to reduce any danger of confusing the connection interfaces, these can also have a characteristic geometric form in each case. The interfaces 9 can also be configured for wireless transfer of data.

The ultrasound block G is provided for recording and processing ultrasound data. Ultrasound data which is recorded using the ultrasound measuring head G1 is transferred to the ultrasound signal processing unit G3 for handling and post-processing. The transfer of the ultrasound data takes place via a signal cable or a wireless connection 7. An ultrasound image which has been computed using the ultrasound signal processing unit is displayed to a user on the monitor 3 of the display B2. With the help of the ultrasound images, internal organs, tissue structures, in particular blood vessels and the like can be examined in a patient. It is possible to detect internal injuries, tissue changes, myocardial infarctions, etc. The clinical status of a patient can be examined particularly accurately and it is possible to produce reliable and accurate diagnoses. The diagnostic reliability and diagnostic accuracy can be increased by using physiological data. It is possible to achieve high-quality primary medical care for a patient in an emergency. In particular, the imaging by means of ultrasound allows imminent or silent myocardial infarctions to be detected, even if no clinically clear symptoms can be found using the electrocardiograph.

The ultrasound block G or parts thereof can be permanently attached in or on the housing 2 of the defibrillator 1, or detachably attached according to a modular construction. In the housing 2 of the defibrillator 1, a receptacle can be provided for holding a coupling substance for coupling a contact surface of the ultrasound measuring head G1 to an examination object. A tube type connection between the defibrillator 1 and the ultrasound measuring head G1 can be provided for carrying the coupling substance to the ultrasound measuring head G1. The coupling substance can be carried to the contact surface via the tube type connection by activating a manual or electric pump or the like. The coupling substance can also be contained in a receptacle which is provided in the ultrasound measuring head G1, and be carried from there to the contact surface. As a result of providing the coupling substance with the defibrillator 1 or the ultrasound measuring head G1, it can be ensured that a certain amount of coupling substance is always carried with the defibrillator 1 and that the ultrasound device is quickly ready for use.

The defibrillation control unit F1 for controlling the high-voltage unit F2 and the delivery of an electric shock is provided in the defibrillation block F. A high voltage which is generated by the high-voltage unit F2 can be delivered to a patient in the form of an electric shock via the defibrillator electrodes F3. In order to reduce the danger of an unintentional delivery of an electric shock, initiator switches F4 are provided at the defibrillator electrodes F3. An electric shock can only be delivered via the defibrillator electrodes F3 if both initiator switches F4 are activated. The defibrillation block F also features a synchronization unit F5 for synchronizing delivery of an electric shock with the heart rhythm of a patient. The synchronization unit F5 is connected to the signal processing unit E1 or the electrocardiograph of the patient monitoring block E and the defibrillator control unit F1. Heart rhythm data or data which is derived therefrom is transferred to the synchronization unit F5. The synchronization unit F5 interacts with the defibrillation control unit F1 such that when the initiator switches F4 are depressed the delivery of an electric shock via the defibrillator electrodes F3 takes place synchronously in relation to the heart rhythm.

The patient monitoring block E and the ultrasound block G are electrically isolated from the high-voltage unit F2. If there is a defect, e.g. in electrically conductive parts of the ultrasound measuring head, the electrodes and sensors etc., any danger to the user or a patient from high voltages is avoided.

In order to allow control and/or operation of the defibrillator 1 by a user, various functions are made available by means of the input/output block C. The functions are divided into a plurality of menus. A defibrillator menu C1 including functions which are specifically required for a defibrillation is provided for controlling the defibrillation block F. Independently of this, a patient monitoring menu C2 and an ultrasound menu C3 are provided for the patient monitoring block E and the ultrasound block G respectively. As a result of such subdivision into different menus, a particularly simple operation and handling of the defibrillator can be achieved and user guidance can be provided. The danger of incorrect operation can be reduced.

The display B2, in particular the monitor 3, which is provided in the display block B can be used universally. Ultrasound images, patient data, physiological data such as e.g. cardiac electric activity, defibrillation data, etc. can be displayed on it. The display of a specific type of data can take place in an area of the display B2, which area is permanently preset for this purpose. The display B2 can be configured in a particularly clear manner. However, it is also possible to display overlay images including different types of data. The size of the area is preferably adapted to the relevant information content of the data and can be made bigger or smaller if required.

The monitor 6 can be a touch-sensitive screen for manually initiating functions of the blocks A to H, e.g. of the defibrillation block F, the ultrasound block G and the patient monitoring block E. In this case, the input/output block (C) at least partially forms a sub-block of the display block B. Alternatively or additionally, push buttons, rotary knobs, switches, etc. can be provided for operation and/or control.

Alternatively, the display control unit B1, the signal processing unit E1, the ultrasound signal processing unit G3 and/or the defibrillator control unit F1 can be contained in the microprocessor block A. For this, the microprocessor block A can contain one or more processors, digital circuits, etc.

During treatment of a patient, the manually or automatically initiated functions and the captured data are stored at least partially or as required in the memory block D. A division of the memory block D into different areas is essentially optional. For reasons of clarity, a first memory area D1 can be provided for storing physiological data and a second memory area D2 for storing ultrasound data. In order to allow the stored data to be transmitted to a data processing system in e.g. a hospital, provision can also be made for a data interface in the input/output block. Such a data interface can also be used in order to transfer software data for operating and controlling the defibrillator and/or the ultrasound device and/or the patient monitoring unit. Further interfaces can be provided for communicating and/or exchanging data with external peripheral devices such as e.g. printers, medical examination devices and the like. An exchange of data preferably takes place via a USB, RF232, radio, infrared, or Firewire interface.

The input/output block C can comprise a transponder, preferably an RFID transponder. Data for the unambiguous identification of the defibrillator can be stored on the transponder. The transponder can contain technical data relating to the defibrillator, e.g. service intervals, functional data, etc. If a locally installed readout system for transponders is available, the location or current point of use can be determined and tracked with reference to the transponder.

The input/output block C can also include a readout unit for reading out information which is stored on a further transponder. Patient data can be read out using the readout unit. In this case, a transponder which is assigned to the patient must be available. In a hospital, the transponder can be attached e.g. to the patient bed or to an armband of the patient. The patient data can be linked to the data of the patient which is stored in the memory block D. This allows an unambiguous assignment of the stored data to a patient.

The input/output block C can additionally feature a card reader for reading out patient data which is stored on a memory of a patient card. Using the card reader, it is possible to read out e.g. patient data from a conventional sickness insurance card. The patient data can be stored in the memory block D if required, linked with data which has already been stored, or used as a basis for identifying data of a patient which is yet to be stored.

The input/output block C can include a communication entity such as e.g. a mobile telephone, a fax device, a modem and the like. An emergency call entity can be additionally provided for simple and rapid generation and transmission of an emergency call signal.

The input/output block C can include a satellite-based navigation system for determining the position of the defibrillator. The navigation system can be used for determining the location of the defibrillator and for providing route guidance for a user. In order to allow particularly reliable navigation of a user, provision can be made such that the navigation system can also receive position information via a radio connection with local, permanently installed node points. A transfer of position data via the radio connection is particularly advantageous if satellite-based navigation is not possible, e.g. in underground subway stations, hospitals, etc.

Using the claimed defibrillator, it is possible to examine clinical conditions particularly accurately and effectively and to produce dependable diagnoses. The defibrillator allows an examination of internal organs, tissues and blood vessels etc. The ultrasound entity proves to be particularly advantageous in the diagnosis of cardiac arrests, ventricular fibrillation, irregular heart rhythms or myocardial infarctions. Myocardial infarctions which are silent or which cannot be detected by means of electrocardiography can be detected using the ultrasound device. In particular, primary medical care can be significantly improved in the case of a medical emergency.

The invention claimed is:

1. A mobile defibrillator used in a medical procedure, comprising:
    a housing;
    an imaging ultrasound device integrated arranged on a top side of the housing of the debrillator;
    a receptacle for holding a coupling substance for coupling a contact surface of a ultrasound measuring head of the imaging ultrasound device to an examination object;
    a data interface that exchange data with a data processing system;
    a connection interface that connects an accumulator to a charge station;
    an entity comprising an electrocardiograph, a thermometer, a blood pressure measuring entity provided in or on the housing for capturing, processing, or representing physiological data of a patient;
    a sensor unit comprising corresponding electrodes of the entity for capturing the data;
    an interface that is assigned an unambiguous color code and has a characteristic geometric form for connecting the electrodes; and
    a monitor having a touch-sensitive screen for manually initiating a function of the defibrillator or the ultrasound device,
    wherein the mobile defibrillator is configured to stay outside of the examination object, and
    wherein an electrical isolation of an electrically conductive element of the ultrasound device from defibrillator voltages or voltages of an electricity network which is connected to the defibrillator is provided.

2. The mobile defibrillator as claimed in claim 1, wherein the monitor displays an image.

3. The mobile defibrillator as claimed in claim 1,
    wherein the ultrasound device has a measured data processing unit to process measured data, and
    wherein the measured data is transferred between the ultrasound measuring head and the measured data processing unit via a wireless connection.

4. The mobile defibrillator as claimed in claim 1, wherein the receptacle is connected to the ultrasound measuring head via a tube for carrying the coupling substance to the ultrasound measuring head.

5. The mobile defibrillator as claimed in claim 1, wherein a pump is provided for automatically supplying a predetermined amount of the coupling substance to the contact surface.

6. The mobile defibrillator as claimed in claim 1, wherein the entity is selected from the group consisting of: electrocardiograph, blood pressure measuring entity, and thermometer entity.

7. The mobile defibrillator as claimed in claim 6, wherein an electrical isolation of an electrically conductive element of the entity from defibrillator voltages or voltages of an electricity network which is connected to the defibrillator is provided.

8. The mobile defibrillator as claimed in claim 1, wherein a connection interface is provided for connecting an accumulator to a charge station for supplying energy.

9. The mobile defibrillator as claimed in claim 1, wherein a data interface is provided for exchanging data with a data processing system, the data interface selected from the group consisting of: USB, RS232, radio, infrared, and Firewire.

10. The mobile defibrillator as claimed in claim 1, wherein at least part of an outer layer of the defibrillator is made from a material featuring a metallic particle, the particle having an average diameter of less than 100 µm in order to screen against an external electromagnetic field of an electronic functional element of the defibrillator.

11. The mobile defibrillator as claimed in claim 10, wherein the particle has an average diameter of less than 100 nm.

12. The mobile defibrillator as claimed in claim 1, wherein a transponder is provided.

13. The mobile defibrillator as claimed in claim 12, wherein the transponder is an RFID transponder.

14. The mobile defibrillator as claimed in claim 12, wherein a readout unit is provided for reading out information which is stored on a further transponder.

15. The mobile defibrillator as claimed in claim 14, wherein a card reader is provided for reading out patient data which is stored in a memory on a patient card.

16. The mobile defibrillator as claimed in claim 1, wherein a communication device is provided for transferring information via a telephone connection, the communication device selected from the group consisting of: mobile telephone, fax device, modem.

17. The mobile defibrillator as claimed in claim 16, wherein an emergency call entity is provided for generating and sending an emergency call signal.

18. The mobile defibrillator as claimed in claim 1, wherein a navigation system is provided for determining a position of the defibrillator.

19. A mobile defibrillator used in a medical procedure, comprising:
   a housing comprising:
      a microprocessor unit,
      a display unit,
      an input/output unit,
      a memory unit,
      a patient monitoring unit,
      a defibrillation unit;
   an imaging ultrasound device arranged on a top side of the housing of the defibrillator defibrillator;
   a receptacle for holding a coupling substance for coupling a contact surface of a ultrasound measuring head of the imaging ultrasound device to an examination object;
   a data interface that exchange data with a data processing system;
   a connection interface that connects an accumulator to a charge station;
   an entity comprising an electrocardiograph, a thermometer, a blood pressure measuring entity provided in or on the housing for capturing, processing, or representing physiological data of a patient;
   a sensor unit comprising corresponding electrodes of the entity for capturing the data;
   an interface that is assigned an unambiguous color code and has a characteristic geometric faun for connecting the electrodes; and
   a monitor having a touch-sensitive screen for manually initiating a function of the defibrillator or the ultrasound device,
   wherein the microprocessor unit, the display unit, the input/output unit, the memory unit, the patient monitoring unit, the defibrillation unit, and the imaging ultrasound device are operatively connected via a bus cable for transferring data, and
   wherein the mobile defibrillator is configured to stay outside of the examination object,
   wherein an electrical isolation of an electrically conductive element of the ultrasound device from defibrillator voltages or voltages of an electricity network which is connected to the defibrillator is provided.

\* \* \* \* \*